United States Patent [19]

Shimizu et al.

[11] Patent Number: 5,512,137
[45] Date of Patent: Apr. 30, 1996

[54] METHOD AND APPARATUS FOR MEASURING CONTAMINATING IMPURITIES IN PULP SLURRY

[75] Inventors: Yasubumi Shimizu; Shozo Morinaga, both of Tokyo, Japan

[73] Assignee: Nippon Paper Industries Co., Ltd., Tokyo, Japan

[21] Appl. No.: 363,919

[22] Filed: Dec. 27, 1994

[30] Foreign Application Priority Data

Dec. 28, 1993 [JP] Japan .................... 5-335431

[51] Int. Cl.$^6$ .................... G01N 21/89; D21F 7/00; G01B 11/28
[52] U.S. Cl. .................... 162/198; 162/262; 162/263; 356/36
[58] Field of Search .................... 162/198, 262, 162/263; 356/36

[56] References Cited

U.S. PATENT DOCUMENTS 4,897,159  1/1990  Bone et al. .................... 162/260

FOREIGN PATENT DOCUMENTS 61-272639  12/1986  Japan .
63-295946  12/1988  Japan .
4-117668   5/1992   Japan .

*Primary Examiner*—David L. Lacey
*Assistant Examiner*—Jose A. Fortuna
*Attorney, Agent, or Firm*—Burns, Doane, Swecker & Mathis

[57] ABSTRACT

A method and apparatus for detecting impurities in raw pulp slurry at high precision using samples on-line. The pulp slurry is passed through a flat mesh wire to accumulate pulp fiber on the wire surface and prepare a wet mat, after which the surface of the wet mat is detected by a CCD camera in a catoptric system while pressed against a flat transparent plate, and the image is processed to measure the area of impurities per unit area of the wet mat.

15 Claims, 4 Drawing Sheets

METHOD AND APPARATUS FOR MEASURING CONTAMINATING IMPURITIES IN PULP SLURRY

BACKGROUND OF THE INVENTION

1. Field of the Invention

The present invention relates to a method for immediate and high-precision detection of impurities which contaminate raw pulp slurry during raw pulp processing, as well as an apparatus therefor.

2. Description of the Related Art

Pulp used in paper making is subject to contamination by impurities such as dirt, pitch, or ink or toner residue. These impurities cause trouble during the paper making process and their contamination lowers the quality of the product. Control of impurities is therefore necessary during the raw pulp processing. Usually, the raw material is periodically sampled to prepare a hand-made sheet, and the production process is controlled by the operator's visual determining of the contaminating impurities. The present applicant has already proposed a dirt measuring device using hand-made sheets (Japanese Patent Application No. 4-117668). There have also been developed an on-line measuring device for use during raw material processing (Japanese Unexamined Patent Publication No. 63-295946) and a method for measuring slurry pulp (Japanese Unexamined Patent Publication No. 61-272639).

Although the above-mentioned dirt measuring device using hand-made sheets provides highly precise measurements, time is required to prepare the hand-made sheets, leading to increased risk of damage to the sheets because of the delay for control during the raw material processing. On the other hand, in the case of the on-line measuring device used during the raw material processing, the setting location is limited to being on the drum-washer filter, and the poor condition of the measuring surface of the raw pulp on the drum-washer filter produces a crude measuring limit, making it impossible to obtain a satisfactory resolution. Furthermore, in the method for measuring slurry pulp, it is necessary to prepare a constant predetermined-dilution raw pulp concentration and flow rate for the measurement, and thus time is required for pretreatment prior to the measurement.

SUMMARY OF THE INVENTION

The object of the present invention is to improve the weaknesses of the conventional methods described above, by providing a method and apparatus capable of detecting impurities in raw pulp slurry at a high precision by taking samples on-line.

The method of measuring impurities according to the present invention is characterized by using wire having a mesh capable of passing through the moisture and trapping the fibrous portions of raw pulp slurry at various concentrations, at the time of raw pulp processing during the step of pulp production or paper making, and suctioning the pulp slurry from the back side of the wire or pressing the wire itself against the pulp slurry, to prepare a highly dense wet mat concentrated on the front of the wire, and then pressing a flat transparent plate on the surface of the wet mat, detecting the surface of the resulting highly dense, highly smooth wet mat with a CCD camera in a catoptric system Via a glees plate, and creating an image therefrom to measure the area which contains impurities with respect to the surface area of the wet mat.

In addition, the apparatus for measuring contaminating impurities in pulp slurry according to the present invention is characterized by having an elongated container having a rectangular or circular cross-section at least a portion of the bottom of which is formed of a flat glass plate which permits visual observation of the interior thereof, and a pulp slurry intake conduit connected to the top of the container and a pulp slurry discharge conduit connected to the bottom via a bulb, with flat wire having a mesh which passes through the moisture in the pulp slurry and is capable of trapping the fiber portion set so as to be vertically movable while in close contact with the side wall of the container; and by being provided with a CCD camera directed from outside of the container toward the above-mentioned plate, as well as a computer for processing the image from the CCD camera in order to measure the area of impurities per unit area of the wet mat.

The transparent plate used here may be a synthetic resin plate, but a glass plate is also suitable.

DESCRIPTION OF THE PREFERRED EMBODIMENTS

The measuring method of the present invention is carried out by preparing a wet mat in a container and making the measurement with this wet mat pressed against a flat transparent plate, and therefore although the image observed over the transparent plate is that of the wet mat, the mat is clearly seen in the same state as after drying. Furthermore, since the measurement is made while in the state of a wet mat, the preparation thereof is simple, and the prepared mat may also be easily returned to the pulp slurry state.

Figure 1:
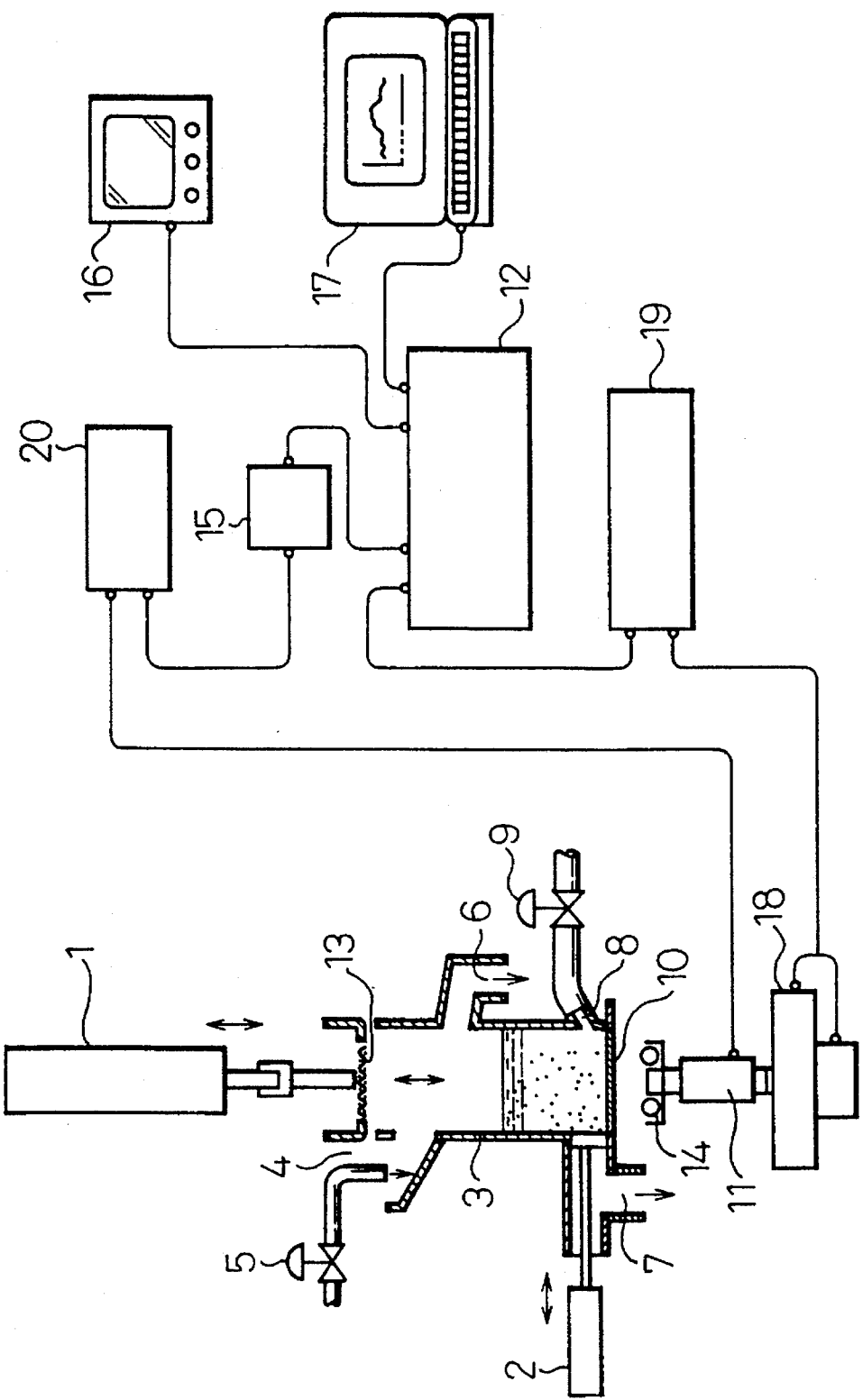
FIG. 1 is an illustration showing a measuring method according to an embodiment of the present invention.
Figure 2:
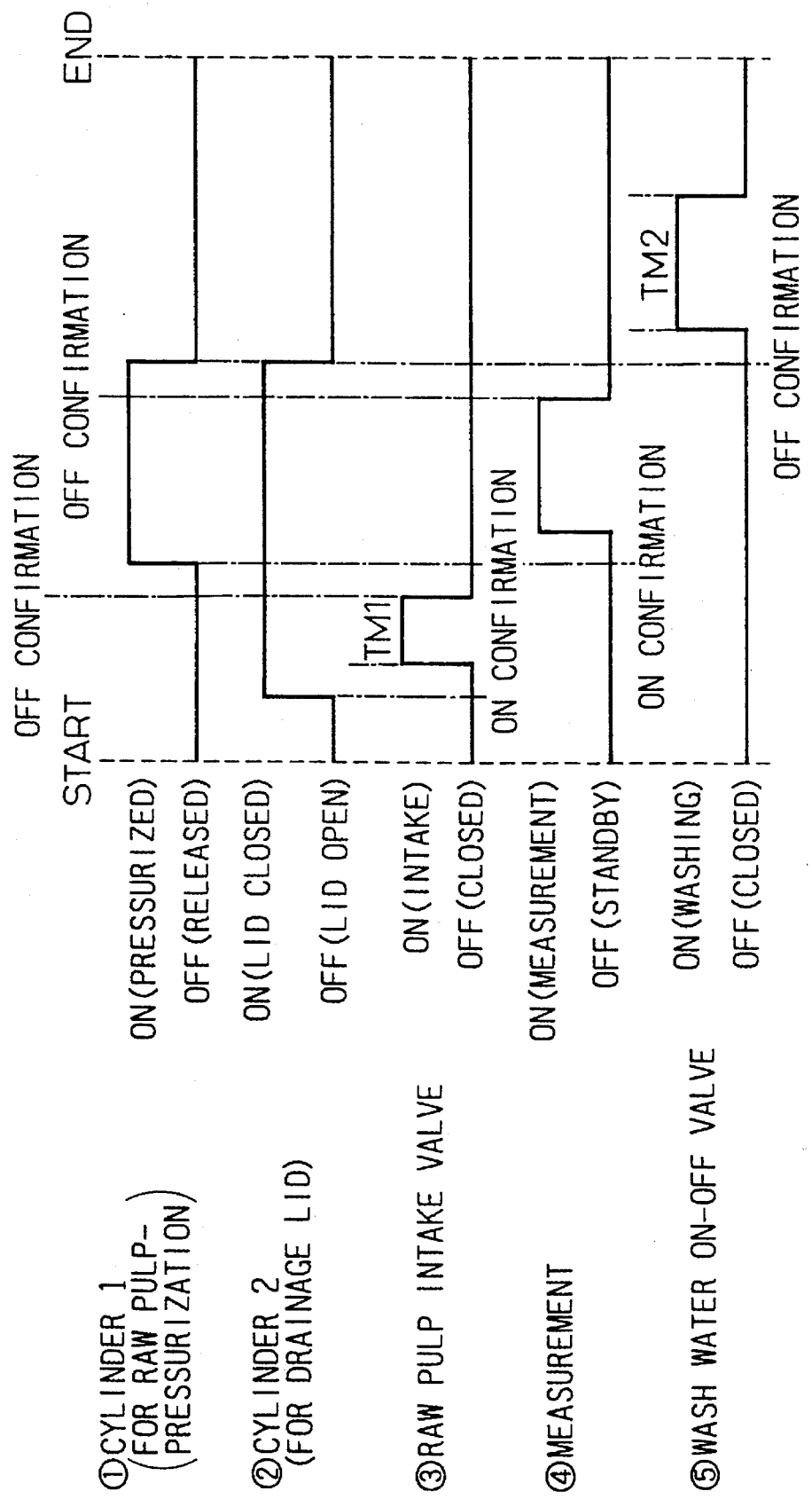
FIG. 2 is a timing chart for the measuring apparatus according to the embodiment.

The measuring apparatus shown in FIG. 1 has an elongated container at least a portion of the bottom of which is formed of a flat glass plate which permits visual observation of the interior thereof, and a pulp slurry intake conduit and a pulp slurry discharge conduit are connected thereto; thus, as shown in the timing chart in FIG. 2, in this apparatus, first the drainage lid cylinder 2 is switched ON to close the lid, the raw pulp intake valve is switched ON to introduce the pulp slurry into the container, and the continuous raw pulp pressurizing cylinder 1 is switched ON to move the wire through the pulp slurry and prepare the wet mat. In this state, the condition of the surface of the wet mat is measured, after which the raw pulp-pressurizing cylinder 1 is switched OFF and released while the drainage lid cylinder 2 is simultaneously switched OFF to open the lid, and the wet mat returns to pulp slurry and is discharged from the drainage valve. Then, the wash water on-off valve is turned ON (opened) and OFF (closed) to introduce a constant amount of water into the container to wash the container. Since one measurement may be made by one such cycle, measurement is possible on-line during the paper making process.

The method and apparatus of the present invention will now be explained with reference to the drawings. FIG. 1 is an illustration showing an embodiment of the present invention. The pulp slurry to be measured is fed from a line pipe or a tank (neither shown) during the paper making step and, by the operation of a bulb, is taken into an elongated container 3 for measurement. This container 3 has a raw pulp intake opening 4 and an overflow outlet 6 for excess sample at the upper end, and it has an on-off sample discharge opening 7 and a wash opening 8 at the lower end, while the bottom is provided with an observation window consisting of a transparent plate 10 to allow observation of the raw pulp from the bottom. In addition, the inside of the Container 3 is provided with mesh wire 13 in close movable contact with the inner wall of the container due to the movement of the piston of a raw pulp-pressurizing cylinder 1. Furthermore, a CCD camera 11 is positioned opposite the above-mentioned transparent plate 10, and it is connected to a CPU 12 which processes the image from the CCD camera 11 and measures the area of impurities per unit area of the wet mat. In addition, illumination 14 is positioned facing the transparent plate 10 for a satisfactory photographic image of the CCD camera 11, while the CCD camera 11 is connected to the CPU 12 via an impurity counting board 15, and a monitor TV 17 and host computer 16 are also connected to the CPU 12. In cases where the image of the wet mat is detected while moving the CCD camera 11, the camera 11 is mounted on an XY stage 18 and controlled by an XY stage controller 19 which controls its movement in the XY direction. In the figure, 20 indicates a power source for the camera.

A method of measurement using the above-mentioned apparatus will now be explained. First, after pulp slurry is introduced into the container 3, pressure is applied to the piston of the raw pulp-pressurizing cylinder 1 to push the mesh wire 13, and the pulp fiber is compressed at the bottom of the container 3 to form a wet mat. The surface of the wet mat prepared in this manner is then detected by the CCD camera through the transparent plate 10 at the bottom of the container. The CCD camera 11 measures the impurities by a catoptric system, but the lens system may be set to match the resolution of measurement, allowing easy detection of impurities on the order of $\phi 10\mu m$.

Also, if the CCD camera is set on an XY stage, a large measurement area may be taken even when a fine resolution of measurement makes the area of a single measurement smaller, as the measurement may be made while moving the XY stage. After the measurement the piston is raised, the discharge opening is opened, and wash water is introduced into the cell (i.e., elongated container) to discharge the pulp. By continuously performing this process, continuous on-line measurement of impurities may be made during the raw pulp processing. The results of the measurement are obtained by sending the image signal taken by the CCD camera 11 to the impurity counting board 15 at high speed for processing, from which it is passed through the CPU 12 at the measuring device end and sent the monitoring host computer. The host computer 16 gives the operating instructions for each of the measuring sections while displaying the results of measurement, i.e. the changes in contamination by dirt, on a trend screen.

Figure 3:
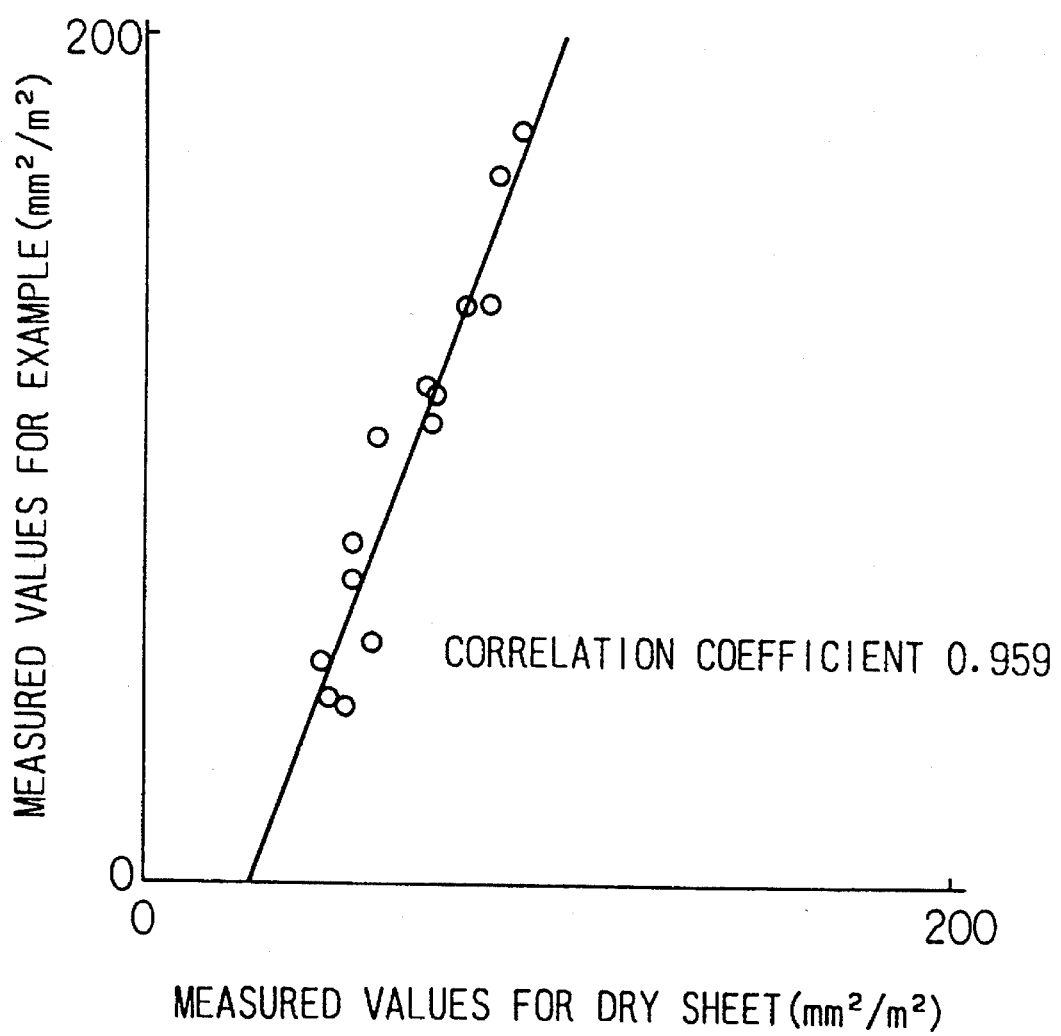
FIG. 3 is a drawing showing the correlation between the results of the method according to the embodiment and a conventional dry sheet measuring method.

FIG. 3 is a drawing showing the correlation between the results of actually measuring impurities in raw pulp slurry by the measuring method described above and the results of measuring impurities in the same raw pulp slurry by the method in Japanese Patent Application No. 4-117668 using a hand-made dry sheet. The measurement using a dry sheet and the method of the present invention are thus seen to correlate very well. Also, Table 1 gives a comparison between the results of measuring impurities based on the density and volume of the raw pulp measured. The bottom area of the cell or elongated container used in this case was 100 mm×100 mm, but as long as there is a constant amount or more of pulp which accumulates at least to a degree where the surface of the wire cannot be seen, so that a uniform wet sheet is thus formed, then it is possible to always detect a constant degree of contamination by impurities per measured area, without depending on the concentration or amount of the slurry itself.

TABLE 1

| Pulp density | Dirt measurement values with different pulp densities and volumes | | |
|---|---|---|---|
| | Pulp volume | | |
| | 6 g | 5 g | 4 g |
| 3% | 54.35 | Poor measurement | Poor measurement |
| | 56.24 | 53.74 | Poor measurement |
| 2% | 55.56 | 56.77 | Poor measurement |
| | 55.67 | 53.32 | 52.75 |
| 1% | 53.35 | 55.75 | Poor measurement |
| | 54.87 | 55.12 | 53.88 |
| 0.5% | 54.22 | 53.24 | 54.87 |
| | 53.37 | 55.02 | 53.71 |

Cell used had a bottom area of 100 m × 100 m
* Poor measurement resulted when a wet sheet did not form well, causing gaps, etc.

Figure 4:
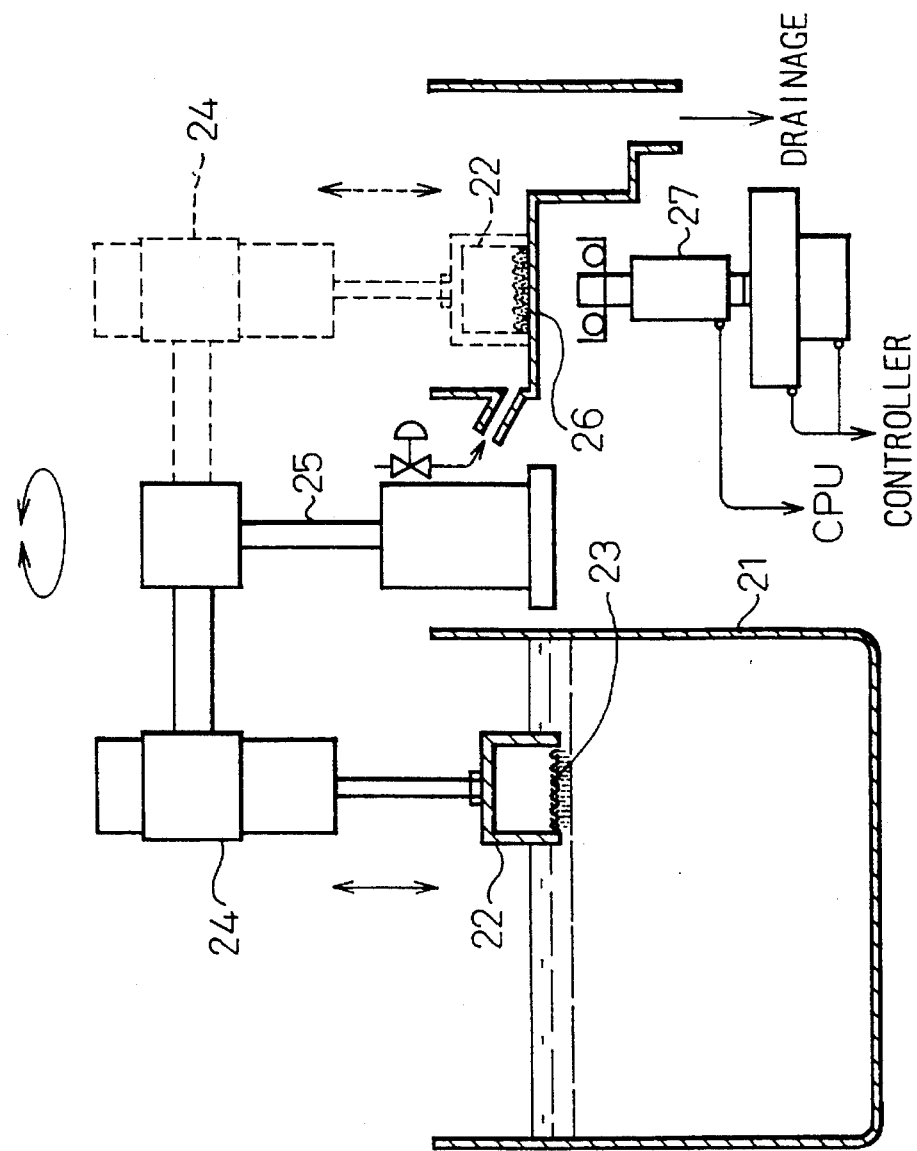
FIG. 4 is an illustration showing a measuring method according to another embodiment of the present invention.

The measuring system in FIG. 4 will now be explained as a separate embodiment. This measuring system has a suction box 22 whose suction side is formed into a mesh wire structure, and the mesh wire 23 passes through moisture of the pulp slurry while trapping the fiber portion, thus forming a wet mat on the surface of the mesh wire 23.

The wet mat formed by suction while the suction box 22 is directly immersed in the pulp slurry in the raw pulp tank 21 is then moved by a vertical cylinder mechanism 24 and rotating frame 25 which manipulate the box, to the position indicated by dotted lines, where it is pressed against a smooth transparent observation window 26. The smooth surface of the wet sheet obtained in this manner is then measured through the observation window 26 by a catoptric system which includes a CCD camera 27. The imaging and display of results is carried out in the same manner as the system described above relating to FIG. 1. After the measurement, the box 22 is raised and wash water is sent to the inside of the box and the measuring surface to wash the sheet on the surface of the box and the measuring surface. By repeating this process, continuous on-line measurement of impurities may be made during the raw pulp processing. In addition, more measurements may be made by mounting a plurality of suction boxes on the rotating frame and conducting simultaneous sampling and measurement.

The mesh wire used in the preceding example is 200 mesh wire, which is for measurement of foreign matter of $\phi 10\mu m$, but the mesh may be selected depending on the size of the foreign matter to be measured. Also, since stable results are achieved only if the pulp concentration of the wet mat used for measurement is at least 20 wt %, the pressure of the pressurizing cylinder must be adjusted so as to adequately produce this concentration.

According to the present invention, highly precise control of impurities in pulp slurry is made possible on-line during the paper making process, allowing real-time evaluation of raw pulp; as a result, unusable raw pulp may be removed prior to or during the paper making step, thus preventing the production of defective paper.

What is claimed is:

1. A method of measuring contaminating impurities in pulp slurry, comprising introducing pulp slurry into a container which has associated therewith a mesh wire, effecting relative movement between the pulp slurry in the container and the mesh wire to permit moisture in the pulp slurry to pass through the mesh wire while trapping fibrous portions of the pulp slurry on the mesh wire to form a wet mat, pressing the wet mat against a flat transparent plate, taking an image of a surface of the wet mat through the transparent plate with a CCD camera, and processing the image taken by the CCD camera to measure impurities per unit area of the wet mat.

2. The method according to claim 1, wherein said step of effecting relative movement between the pulp slurry and the mesh wire includes moving the mesh wire within the container so that the mesh wire moves towards a bottom of the container.

3. The method according to claim 1, wherein said step of effecting relative movement between the pulp slurry and the mesh wire includes utilizing suction to draw the pulp slurry against the mesh wire.

4. The method according to claim 1, wherein said transparent plate is located at a bottom of said container and the step of pressing the wet mat against the transparent plate includes moving said mesh wire within said container to press the wet mat against the transparent plate.

5. The method according to claim 1, wherein said transparent plate is located exteriorly of said container, the method including removing the mesh wire from the container after formation of the wet mat on the mesh wire, and thereafter moving the mesh wire towards the transparent plate to compress the wet mat.

6. An apparatus for measuring contaminating impurities in pulp slurry, comprising an elongated container having a bottom, a side wall and an interior for receiving pulp slurry, at least a portion of the bottom of the container being formed as a flat transparent plate which permits visual observation of the interior of the container, a pulp slurry intake conduit connected to a top of the container, a pulp slurry discharge conduit connected to the bottom of the container, a vertically movable wire mesh which permits passage of moisture in the pulp slurry and traps fibrous portions of the pulp slurry, said mesh wire being in sealed contact with the side wall of the container, a CCD camera positioned and arranged so as to be directed from outside of the container toward said plate to produce an image of a surface of the wet mat pressed against the transparent plate, and a computer for processing the image from the CCD camera to measure impurities per unit area of the wet mat.

7. The apparatus of claim 6, including a wash water intake conduit connected to said elongated container.

8. The apparatus according to claim 6, including a sample discharge opening located adjacent the bottom of the cylinder.

9. A method of measuring contaminating impurities in pulp slurry, comprising, after introduction of pulp slurry into an elongated container having a bottom at which is located a flat transparent plate, lowering into said container a mesh wire which permits passage of moisture and traps fibrous portions of the pulp slurry to accumulate pulp fiber on the mesh wire and form a wet mat, pressing against the flat transparent plate a surface of the wet mat, taking an image of the surface of the wet mat through the transparent glass with a CCD camera, and processing the image taken by the CCD camera to measure impurities per unit area of the wet mat.

10. The method according to claim 9, including introducing wash water into the cylinder after measurement of the impurities in the wet mat.

11. An apparatus for measuring contaminating impurities in pulp slurry, comprising a container for receiving pulp slurry, a mesh wire positioned and arranged with respect to the container for permitting passage of moisture in the pulp slurry and for trapping fibrous portions of the pulp slurry on the mesh wire, means operatively associated with respect to mesh wire for effecting relative movement between the mesh wire and the pulp slurry in the container to cause moisture to pass through the mesh wire while trapping fibrous portions of the pulp slurry on the mesh wire, a transparent plate positioned and arranged so as to have pressed thereagainst by the mesh wire a wet mat which is formed through accumulation of fibrous portions on the mesh wire, a CCD camera positioned and arranged so as to be directed toward said transparent plate for producing an image of the wet mat pressed against the transparent plate, and a computer operatively associated with the CCD camera for processing an image from the CCD camera to measure impurities in the wet mat.

12. The apparatus according to claim 11, wherein said transparent plate is positioned exteriorly of said container.

13. The apparatus according to claim 11, including drive means operatively associated with the mesh wire for vertically moving and rotating the mesh wire between one position in which the mesh wire is positioned in the container and another position in which the mesh wire is positioned adjacent the transparent plate.

14. The apparatus according to claim 11, wherein said means for effecting relative movement between the mesh wire and the pulp slurry includes a raw pulp pressurizing cylinder for moving the mesh wire vertically within the container.

15. The apparatus according to claim 11, wherein said means for effecting relative movement between the mesh wire and the pulp slurry includes a suction device.

* * * * *